(12) United States Patent
Storek et al.

(10) Patent No.: US 7,351,592 B2
(45) Date of Patent: Apr. 1, 2008

(54) MICROFLUIDIC DEVICE AND METHOD WITH TRAPPING OF SAMPLE IN CAVITIES HAVING LIDS THAT CAN BE OPENED OR CLOSED

(76) Inventors: David Storek, Golvläggaregatan 4 C, S-412 62 Göteborg (SE); Niklaus Schneeberger, Route des Buchilles 42, CH-2017 Boudry (CH); Robert P. Otillar, Jr., 950 N. San Antonio Rd., #16D, Los Altos, CA (US) 94022; Anatol Krozer, Klamparegatan 5, S-413 Göteborg (SE)

( * ) Notice: Subject to any disclaimer, the term of this patent is extended or adjusted under 35 U.S.C. 154(b) by 401 days.

(21) Appl. No.: 10/248,848

(22) Filed: Feb. 24, 2003

(65) Prior Publication Data

US 2004/0166577 A1    Aug. 26, 2004

Related U.S. Application Data

(63) Continuation of application No. PCT/SE01/01799, filed on Aug. 23, 2001.

(60) Provisional application No. 60/228,015, filed on Aug. 24, 2000.

(30) Foreign Application Priority Data

Aug. 23, 2000  (SE)  ................................ 0002990

(51) Int. Cl.
 *G01N 33/553*  (2006.01)
(52) U.S. Cl. ...................... 436/526; 436/518; 436/524; 422/50; 422/61; 422/68.1; 422/82.01; 422/186; 435/287.1

(58) Field of Classification Search .................. 422/50, 422/61, 68.1, 82.01, 129, 186; 435/7.1, 4, 435/287.1; 436/518, 524, 526
See application file for complete search history.

(56) References Cited

U.S. PATENT DOCUMENTS

| 4,414,243 | A | * | 11/1983 | Cline ......................... 427/100 |
| 4,822,566 | A | * | 4/1989 | Newman .................. 422/82.01 |
| 4,932,255 | A | * | 6/1990 | Brace et al. ............. 73/204.11 |
| 5,235,235 | A | * | 8/1993 | Martin et al. ........... 310/313 D |
| 5,655,665 | A |   | 8/1997 | Allen et al. |

(Continued)

FOREIGN PATENT DOCUMENTS

FR    2781886    2/2000

(Continued)

OTHER PUBLICATIONS

Barnes-Svarney, Patricia, Ed., The New York Public Library Science Desk Reference (MacMillan USA 1995) p. 254.

*Primary Examiner*—Long V. Le
*Assistant Examiner*—Melanie J. Yu (57) ABSTRACT

Method and arrangement (10, 20) for preparing samples (15, 27) submergible in a liquid medium. The arrangement includes a carrier structure (11). The carrier includes a device (13, 23) for controllable generation of a magnetic field through influence of a control signal to attract at least part of the at least first and second type of samples (15, 27) towards specific locations on the carrier when connected to a first control signal and to repel at least one of the first or second type of samples when connected to a second control signal.

31 Claims, 3 Drawing Sheets

U.S. PATENT DOCUMENTS

| | | |
|---|---|---|
| 5,755,942 A | 5/1998 | Zanzucchi et al. |
| 5,814,525 A * | 9/1998 | Renschler et al. ........... 436/524 |
| 5,869,748 A * | 2/1999 | Stevenson et al. ......... 73/53.01 |
| 5,874,219 A | 2/1999 | Rava et al. |
| 5,922,537 A * | 7/1999 | Ewart et al. .................... 435/6 |
| 5,922,617 A | 7/1999 | Wang et al. |
| 5,976,466 A * | 11/1999 | Ratner et al. ............ 422/82.11 |
| 5,981,297 A * | 11/1999 | Baselt ......................... 436/514 |
| 6,161,437 A * | 12/2000 | Brennan et al. ............... 73/655 |
| 6,355,491 B1 * | 3/2002 | Zhou et al. .................. 436/518 |
| 6,358,752 B1 * | 3/2002 | Durst et al. ................. 436/514 |
| 6,468,809 B1 * | 10/2002 | Prinz et al. ................. 436/526 |
| 6,468,810 B1 * | 10/2002 | Korpela ...................... 436/526 |
| 6,572,830 B1 * | 6/2003 | Burdon et al. ......... 422/186.29 |
| 6,630,359 B1 | 10/2003 | Caillat et al. |
| 2002/0001855 A1 * | 1/2002 | Prentiss et al. .............. 436/526 |
| 2002/0086443 A1 * | 7/2002 | Bamdad ...................... 436/526 |
| 2002/0119470 A1 * | 8/2002 | Nerenberg et al. ............. 435/6 |
| 2005/0148101 A1 * | 7/2005 | Bamdad et al. ............. 436/524 |

FOREIGN PATENT DOCUMENTS

| | | |
|---|---|---|
| WO | WO 9615450 A1 | 5/1996 |
| WO | WO 0043534 A1 | 7/2000 |
| WO | WO 00/49382 | 8/2000 |
| WO | WO 0054882 A1 | 9/2000 |
| WO | WO 0060356 A1 | 10/2000 |

* cited by examiner

MICROFLUIDIC DEVICE AND METHOD WITH TRAPPING OF SAMPLE IN CAVITIES HAVING LIDS THAT CAN BE OPENED OR CLOSED

CROSS REFERENCE TO RELATED APPLICATIONS

This application is a continuation patent application of International Application No. PCT/SE01/01799 filed 23 Aug. 2001 which was published in English pursuant to Article 21(2) of the Patent Cooperation Treaty, and which claims priority to Swedish Application No. 0002990-0 filed 23 Aug. 2000 and to U.S. Provisional Application No. 60/228,015 filed 24 Aug. 2000. Said applications are expressly incorporated herein by reference in their entireties.

BACKGROUND OF INVENTION

1. Technical Field of the Invention

The present invention relates to a method and arrangement for enhancing detection of different samples including at least first or second types of samples.

2. Background of the Invention

When considering a living organism, for example a human being, an animal or even a plant, a basic subunit of such organisms is a cell. One way to categorize such cells is by the functions they are aimed to perform in an organism; e.g.: epithelial cells, (skin) muscle cells, neural cells and the like. All these cells communicate with the surrounding world via complex mechanisms, which usually involve many different complex molecules called proteins, some of which are embedded into a cell wall. Cells live and die very much like the whole organism; they also grow, divide, and the like. In all these functions, many different parts/components of a given cell take part. These components can be proteins, enzymes (acting as catalysts for certain reactions occurring in the cell) as well as DNAs, RNAs, tRNAs, and the like. Thus, there exists an enormous number of processes (mutations) occurring in an organism per unit time, and also in each cell of the organism. Some of these mutations are important for the cell-well being, but others are dangerous, for instance, cancerous mutations.

Therefore it is very important to be able to foresee, at least partly, the behavior of a cell, to map out the reactions that occur, and their products (usually creation of new cells DNAs and/or proteins). It is equally important to be able to cure malignant events in the body, which can arise by either invasion of other organisms (viruses or bacteria), or by processes caused within the body itself (autoimmune reactions), or by outside environmental factors such as stress.

In all of these processes, the number of out coming events is immense. Take for example, DNA strands. There are millions upon millions of different DNAs that contribute to production of even larger numbers of proteins whose function and chemistry is far more complex than that of the DNAs themselves.

It would take many lifetimes to establish the structure of even a few thousands of the DNA molecules, not to mention the proteins and/or their functions, or related drugs. Therefore, one needs fast techniques that enable the acquisition of information in parallel, and effective means of storage and handling of such information.

During the past decades, a search to develop such methods has been started. The common name for such techniques has been coined as high throughput screening (HTS). The idea is to prepare, in parallel, fewer samples so as not to use large amounts of expensive and rare chemicals but, to make as many as are feasible, as is possible. The easiest and the most logical (from the information handling point of view) way is to arrange such complex samples in a matrix. Taken from the semiconductor industry, these matrices are often referred to as "chips".

Figure 1:
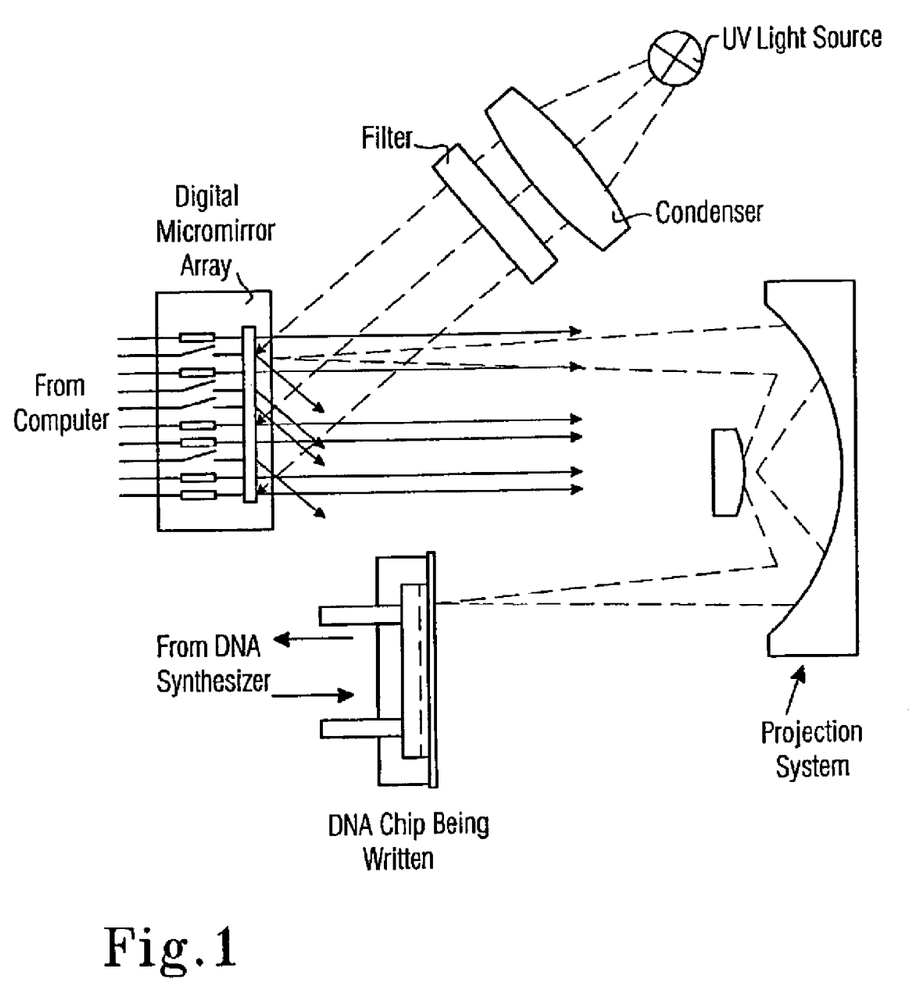
FIG. 1 shows an arrangement of conventional design.

One example of such preparation is given in FIG. 1, *Biophotonics, January/February* 2000, *Univ. of Wisconsin, Franco Cerrina,* et al. According to this technique, a matrix is created by burning away deposits from certain selected places on a chip, while depositing additional chemicals on other places. This method, although fairly fast and cheap, produces a permanent pattern on a matrix which will be used up after a single experiment. Thus, each new experiment requires production of a new matrix.

The number of elements (spots) in a matrix varies depending on the preparation method, but usually does not exceed 10,000; although, matrices as large as including 1,000,000 sites have been reported. The outcome of each single "experiment," therefore, gives at best 10,000 results. In reality this number is much lower (around 20% of best results) due to the very poor quality of even the best matrices produced to date.

Apart from the preparation mentioned above, a complete HTS-system also has to include means of detecting for the events taking place in each spot, as well as data transfer and evaluation.

FR 2,781,886 concerns fabrication of a microsystem with multiple points for chemical or biological analysis consisting of a structure provided with micro-cups. Each micro-cup is designed to receive a reagent coupled with a conductor polymer. Each micro-cup has a receiving electrode whereon, is fixed, the reagent via of the polymer conductor, with which it is coupled. Each micro-cup also has a counter-electrode arranged so as to apply, in a volume of the micro-cup, an electric field between its counter-electrode and its receiving electrode. The structure has means for simultaneously connecting all the receiving electrodes to a first electric potential and means for simultaneously connecting all the counter-electrodes to a second electric potential for generating the electric field.

U.S. Pat. No. 5,874,219 discloses methods for concurrently processing multiple biological chip assays by providing a biological chip plate comprising a plurality of test wells, each test well having a biological chip having a molecular probe array. Samples are introduced into the test wells; subjecting the biological chip plate to manipulation by a fluid handling device that automatically performs steps to carry out reactions between target molecules in the samples and probes. The biological chip plate is subjected to a biological chip plate reader that interrogates the probe arrays to detect any reactions between target molecules and probes.

The International Application No. WO 00/54882 provides electromagnetic chips and electromagnetic biochips having arrays of individually addressable micro-electromagnetic units, as well as methods of utilizing these chips for directed manipulation of micro-particles and microstructures such as biomolecules and chemical reagents. An electromagnetic biochip includes an individually addressable micro-electromagnetic unit chip with ligand molecules immobilized on its surface. By controlling the electromagnetic field at each unit of the array and combining this control with magnetic modification of biomolecules, these chips can be used for directed manipulation, synthesis and release of biomolecules in order to increase sensitivity of biochemical or chemical analysis and reduce assay time. Other advantages with these chips include minimized damages to biological molecules and increased reproducibility of assay results. According to this invention, magnetic forces are used to control and manipulate magnetically modified molecules and particles and to promote molecular interactions and/or reactions on the surface of the chip. However, the drawback is that the detection is not sensitive, as other molecules will also be detected.

SUMMARY OF INVENTION

A main objective of the present invention is to provide an arrangement that improves the "one by one" experimentation through enhancing the detection sensitivity.

The technique allows a relatively rapid screening of new chemicals to be used as drugs, both with regard to their function and, importantly, with regard to the determination of the side effects that a given drug might exert. The technique can also be used in many other applications such as genome determination, proteomics and others.

In an arrangement configured according to the invention, it is relatively easy to change both the dimensions and the number of the wells. Also, the simplicity of the design will allow integrating the reaction product detection system, on-chip, and perhaps also the facility for multi-well deposition of the active substance.

Another object of the invention is to describe how the detection limits for the events under study can be improved using techniques similar to those used for chip production.

These objects are achieved by the above-described arrangement that includes at least first or second type of samples, and having a carrier structure. The carrier includes a device for controllable generation of a magnetic field through influence of a control signal to attract at least part of the at least first and second type of samples towards specific locations on the carrier when connected to a first control signal and to repel at least one of the first or second type of samples when connected to a second control signal.

Preferably, the device is a coil or a magnetically active material and it is made of an electrically conducting material, preferably aluminum. In each device, a current of different strength is applied through a conductor whereby the current amplitude and the number of windings in the coil are proportional to the strength of the magnetic field.

According to a first aspect of the invention, the arrangement includes a cavity provided in a substrate and a lid for closing the cavity. Preferably, the lid is a magnetic bead. The bead is directed onto a cavity using external magnets that create magnetic fields counteracting the field created by the material deposited around each cavity. Each cavity is surrounded by a device, which directs the lid using external magnets that create magnetic fields counteracting the field created by material deposited around each cavity. The cavities are etched in a silicon surface and the lid is provided as a large magnetic particle in the liquid. The particle is attracted to a predetermined cavity when the coil of the cavity is energized by electric current to produce magnetic field of spatial attraction. Before sealing off the cavity, smaller magnetic particles are attracted into the cavity. The sample is a magnetic particle covered with appropriate chemical(s).

In one embodiment, the arrangement includes means for detection of presence of a magnetic capping lid capping a cavity. In one embodiment, the capping is detected by detecting the change in inductance in the control circuit, which produces the attractive magnetic field whereby the bead acts like a magnetic yoke in a transformer, increasing the inductance. In another embodiment, the capping is detected through decrease of electromagnetic radiation to a detector inside the cavity or by changes of capacitance between electrodes inside the cavity or near a cavity rim.

The arrangement may also include means for detection of changes of inductance when a magnetic particle passes through the opening into or out of a cavity. The indication is determined using the direction of externally controlled magnetic field, either by changing the direction of the electric current flowing through a coil or flipping an external magnetic. Preferably, the particle contains particular molecular coating, which reacts with the liquid in that cavity or with the coating adsorbed on the walls of the cavity.

The substrate can be made of silicon, Si, or of Si-compound, such as Si-oxide Si-nitride or Si-carbide, or combinations thereof, or a suitable polymer, such as polyethylene, polyethylene glycol, polyethylene oxide, fluorine containing a polymer (PTFE BTeflon), or silicon containing a polymer.

According to a second aspect of the invention, the arrangement includes a member for generating acoustic waves and the device on a substrate or carrier. The device and the member for generating acoustic waves are covered with an insulating layer. On the insulating layer, a combination of receptor-bead of a magnetizable material is attached. A sample is provided with a magnetic portion, which can be attracted towards the receptor. The combination of receptor-bead attenuates the acoustic wave stronger than receptors attached to the insulating layer. Preferably, the surface of the insulating layer is inert to receptors, and the receptor-bead combination is attached to the surface by magnetic forces acting on the bead.

The invention also relates to a method for analyzing different samples in a analysis arrangement in a fluid medium, the samples being provided with magnetic members. The arrangement includes a carrier structure and a testing section on the carrier structure that is provided with a magnetic field generator upon reception of a control signal. The testing section is provided with a test material reactive to at least one type of the samples.

A method practiced according to the present invention includes attracting the different samples to the testing section by generating a magnetic attraction force and after reaction, repelling samples not being the one type of samples.

Each generator is applied a current of different strength. The arrangement is provided by a cavity in a substrate. The method includes the further steps of arranging a magnetic lid for closing the cavity and directing the bead onto a cavity using external magnets that create magnetic fields counteracting the field created by the material deposited around each cavity. Smaller magnetic particles are attracted into the cavity before being sealing the cavity off. Preferably, the sample is a magnetic particle covered with an appropriate chemical(s).

According to this method, it is possible to detect the presence of a magnetic capping lid capping a cavity. The capping is determined by detecting the change in inductance in the control circuit that produces the attractive magnetic field. In this way, the bead acts like a magnetic yoke in a transformer, increasing the inductance. The capping may also be determined through decrease of electromagnetic radiation to a detector inside the cavity or by changes of capacitance between electrodes inside the cavity or near the cavity rim. According to the method, it is possible to detect changes of inductance when a magnetic particle passes through the opening into, or out of a cavity, thereby determining the indication using the direction of externally controlled magnetic field. This is accomplished either by changing the direction of the electric current flowing through a coil, or flipping an external magnetic.

According to the method, given a known number of samples in each cavity and a density of respective coatings, quantitative data on the number of reactions between the coating on a wall of the cavity and the coating on a small sample is obtained by counting the number of samples.

BRIEF DESCRIPTION OF DRAWINGS

In the following, the invention will be further described in a non-limiting way with reference to the accompanying drawings, in which.

DETAILED DESCRIPTION

A basic idea of the present invention is to present an arrangement which enhances detection and analysis by reducing the number of error sources. Surprisingly, it has been achieved by attracting some samples to a section and repelling the samples not achieved; e.g., a reaction with an agent in the section.

Figure 2:
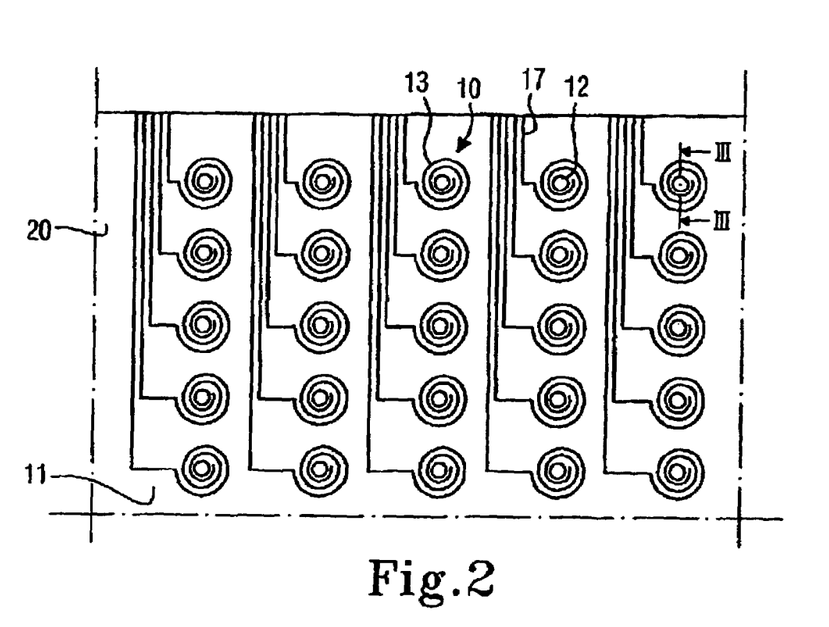
FIG. 2 is a schematic view, from above a chip according to the present invention.
Figure 3:
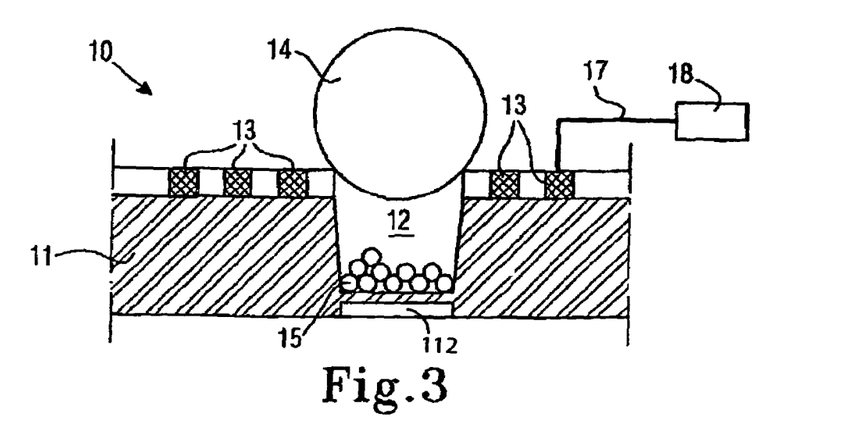
FIG. 3 is a schematic view, showing an enlarged cross-section through a part of the chip along line III-III as depicted in FIG. 2.

FIGS. 2 and 3 illustrate a preferred example of an arrangement configured according to the invention. FIG. 2 illustrates an enlarged schematic view of a part of chip 19 including a number of sample collecting arrangements 10. Each sample collecting arrangement includes a cavity (crater, pocket, or well) 12 provided in a substrate 11, and means 13 to control the cap (lid or cover) 14. Each control means 13 is connected to controller 18 (FIG. 3) through connections 17.

FIG. 3 is a schematic cross-section through the device 10. However, the device 10 is shown in a stage where samples 15 are collected and the crater 12 is closed by means of the lid or closure 14. The samples in this particular case are magnetic particles of diameter(s) much smaller than the diameter of the lid, covered with appropriate chemical(s). In this embodiment, the lid control means 13 include electrically actuated coils and the lid 14 is a magnetizable bead.

By making many craters 12, all with individually controlled lids 14, different types of mixing of solids dispensed in a liquid and/or liquids can be achieved at the same time. As different liquids/solids are introduced to the outside of the craters, only user-selected craters with open lids will be reached for the mixing by the liquids/solids external to the closed craters.

The dimensions and the shapes of each crater 12 can of course vary within a large interval both with respect to its diameter and depth. The craters can have circular cross-section, for example being about 50 um deep with diameters of approximately 100 um. It is relatively easy to produce craters with dimensions ranging from a few um and larger, and with depths ranging from a few um and up to several hundreds of um, in, for example, square shapes.

The material of the substrate can be silicon and the manufacturing process may include micro-machining, similar to the process of making microprocessors or memories chips. A device configured according to the invention may contain from several hundreds of craters on a single piece of silicon, establishing a so-called chip. Of course, tens of thousands of craters on commercial units can be arranged.

Preferably, the lid is a micro-bead introduced in a liquid. The lid-actuation mechanism that is used for the closing and the opening each of the craters can include using switchable magnetic fields that influence the motion of the introduced beads. The magnetic fields are created using the coils 13 deposited around each crater.

The coils 13 surrounding each of the craters are made of an electrically conducting material. In a preferred embodiment, the conductor is made of aluminum, Al, but any electrical conductor can be used. Preferably, each coil is accessible through electrically conducting leads so that a current of different strength can be applied separately to each coil. The current amplitude and the number of windings in the coil are proportional to the strength of the magnetic field, which can thus be varied. Clearly, it is possible to change the number of windings in the coils surrounding each crater as well as their width and thickness within a broad range of dimensions. Preferably, but not exclusively, coils can have from 2 to 10 windings.

In an alternative embodiment, instead of the coils 13, the control means can take the form of a magnetically active material surrounding each crater and which directs the beads using external magnets that will create magnetic fields counteracting the field created by the material deposited around each crater 12.

Preferably, the craters are etched in the silicon surface and the lid is provided by a large magnetic particle 14 in the liquid. Thus, particle 14 can be attracted to the crater of choice when the coil of this crater is energized by electric current to produce magnetic fields for spatial attraction. Before sealing off the crater of choice, however, it is also possible to attract smaller magnetic particles into the crater. To attract the smaller magnetic particles 15 to the crater, the coil is energized by an electric current.

When the coil is energized, a magnetic field is established. This field will attract the magnetic particle 15 from the liquid. These smaller particles have higher mobility in the liquid compared to the mobility of larger particles and will thus reach crater faster then the larger lids. The large lid-particle will cap the crater at a later stage. Preferably, as large particles commercially available magnetic particles such as ferromagnetic or super-paramagnetic having about 100 micrometers in size can be used, while the size of the smaller particles is much smaller than the crater's size. There are other dimensions and particle types on the market and the invention is applicable a broad range of particle sizes, shapes and materials.

To open a closed crater, a repelling field is generated either externally or by inverting the direction of the current flowing through the coil. It is also possible to terminate the current through the coil, whereby the particle may be released due to shear force from the flowing liquid or due to gravitational forces if the craters are positioned "upside down."

The simple actuation of the crater lid using a current controlled magnetic field(s) and the large number of craters on a chip makes it necessary that the chip be operated automatically through a controlling arrangement. The chip is preferably provided with an interface device that establishes electrical connection with the chip and provides the handling of the surrounding fluid with the beads and chemicals. After use, the chip may be removed for cleaning and reuse or disposal. The interface device will be connected to a computer equipped with suitable software to control the sequence of operations on the craters and the liquid handling system. The software will also provide an interface for the user to establish the process sequence and to plan the states of the crater lids in each sequence.

Detection of a magnetic capping bead can also be done. It is important to obtain feedback on which craters are capped. The presence of a magnetic capping bead, in place over a crater, can be detected by the change in inductance in the electric circuit, which produces the attractive magnetic field. The bead acts like a magnetic yoke in a transformer, increasing the inductance. A resonant, or other circuit can then detect this inductance change.

The presence of the capping bead can be detected by various other schemes such as a decrease of electromagnetic radiation experienced by a detector inside the crater, or by changes of capacitance between electrodes inside the crater or near the crater rim.

Each well/crater bottom can be prepared for a particular detection method; for example with glass bottom for optical detection, or crater bottom having deposited electrodes for the capacitance measurements/electrochemical detection.

Another possible application along similar lines is the detection of changes of inductance when a small magnetic sphere passes through the opening into a well. Using this arrangement, according to the invention, it is possible to determine whether a sphere is entering the well, or if it is leaving the well. This is determined using the direction of an externally controlled magnetic field either by changing the direction of the electric current flowing through a coil or flipping an external magnetic field creating device by other means. Such a sphere may contain particular molecular coating, which will react with the liquid in that well or with the coating adsorbed on the walls of the crater. Given that the number of spheres is known in each well, as is the density of the respective coatings, quantitative data on the number of reactions between the coating on the wall and the coating on a small bead can be obtained by simply counting the spheres.

In the following non-limiting examples are given for simplifying the understanding of the invention. According to a first example, liquid A containing magnetic beads is introduced. User selected craters 12 are energized, and hence capped. The remaining beads are flushed away with a cleaning liquid. Now liquid B is introduced, containing small (much smaller than the capping beads) particles, called X, made of a material interesting to the user. Only uncapped craters will accept X. Then, more magnetic beads are introduced and selected craters are capped, trapping X. Cleaning liquid is used to flush all excess away. A liquid containing chemical reagent Y can then be introduced and some craters are opened. X and Y are allowed to mix and react, but only in the user-selected areas. This reaction can be followed using sensing techniques that can easily be incorporated into the system, for example using optical techniques. Other possible novel detection techniques that are easily incorporated into the present embodiment are described below.

The presence of the capping bead can be detected by various other schemes such as a decrease of electromagnetic radiation experienced by a detector (112) inside the crater, or by changes of capacitance between electrodes inside the crater or near the crater rim.

Each well/crater bottom can be prepared for a particular detection method (112); for example with glass bottom for optical detection, or crater bottom having deposited electrodes for the capacitance measurements/electrochemical detection.

Yet another application of the present invention is to lock the cells in the wells filled with different chemicals and monitor the reaction of cells (cell proliferation, differentiation, spreading or others) to these chemistries. This would enable, for example, a fast, high throughput screening of drugs.

The arrangement may also be used separately, one-by-one, for example to deliver a certain chemical, or chemicals, locally at a certain place or places in a reaction vessel, and monitor reaction products locally, or to deliver a drug inside a body.

Another field of possible applications of the device has been triggered by something generally referred to as a "low throughput screening" (LTS). LTS is often used when the amount of required information is smaller, but the researcher wants to additionally obtain some quantitative information about concentrations of analyses or number of reactions that occur during certain time at certain amounts of reagents. The idea behind LTS has much in common with another timely idea often used today and referred to as an "electronic tongue." Electronic tongue is a device that enables one to determine components in a liquid. These components can then be associated with certain tastes (sweet, sour, salt, etc. or combinations thereof). To determine the content of simple liquids in a liquid mixture, for example % of sugar dissolved in a cup of tea along with the amount of tea used to prepare this cup, and even perhaps different tea blends used. To acquire knowledge about all these requires performing several experiments with constituents that react differently to different tea blends and to different amounts of tea from each blend that has been used, as well as to the amounts of sugar being dissolved in this tea. All these can be made by LTS methods using the presently disclosed equipment, and choosing appropriate reagents different for each crater and letting these first react with "standard" samples ("teaching the tongue" to recognize certain non-mixed liquids) and later exposing these samples to mixtures of different tea blends, with or without sugar. Appropriate data processing from the outcome, compared with the results obtained on standard samples, enables one often to obtain information about tea blends used and the amount of sugar dissolved.

The device is not limited to spheres or coils for creation of magnetic fields that direct beads, nor is it limited to the use of beads. Other shapes can be used. Finally, the present invention is not limited to the use of silicon technology to fabricate the crater matrices; other materials can be used for this purpose.

Additional, non-limiting examples are provide below of different crater preparation techniques, and materials of use paired with its utilization. A general concept behind these examples is to manipulate small particles in order to bring them to a chosen place on the surface of the substrate using magnetic field(s) as a driving force for particle manipulation. The surface of the substrate may or may not be patterned in a particular manner. When the substrate is patterned and the pattern consists of craters, some particles are used preferably as caps or lids to close each crater as earlier described. When the substrate is left without a pattern or patterned in a different manner (see below for an example), the particles can be used mainly as a way to enhance sensitivity of detection of the processes taking place in the device.

The magnetic force to manipulate the particles can be created using coils as described above, but it can also be created using externally applied magnets. In the former case, the field strength (and thus the magnitude of the force) is determined primarily by the number of windings in the coil and the magnitude of the electric current passed therethrough. In the latter case it is possible to control the magnitude of the magnetic force by appropriate choice of magnet position and strength.

The substrate may be made of silicon (described above), Si, or of Si-compound, e.g. Si-oxide Si-nitride or Si-carbide, or combinations thereof. It may also consist of thin self-supporting Si, or of a Si-compound, with another film of suitable thickness (for example few micrometers), such as ZnO, evaporated onto its surface. This additional film is needed if the device is to work as an acoustic wave device for detection.

The substrate may also be fabricated using other material than silicon. For example, a suitable polymer, e.g. polyethylene, polyethylene glycol, polyethylene oxide, fluorine containing a polymer (PTFE BTeflon), or silicon containing a polymer may be used as a substrate material.

When patterning, the different substrate techniques may be used depending on the substrate material and the pattern. Thus, Si and Si-compounds are suitably patterned applying techniques known from semiconductor fabrication. When patterning polymers, one can use known techniques like polymer stamping or moulding.

Figure 4:
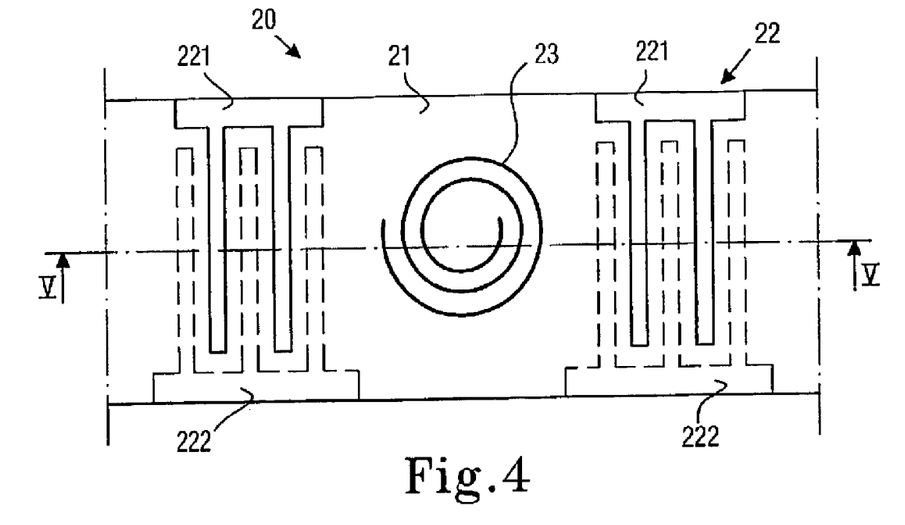
FIG. 4 is a schematic view from above of a part of another chip according to the invention.
Figure 5:
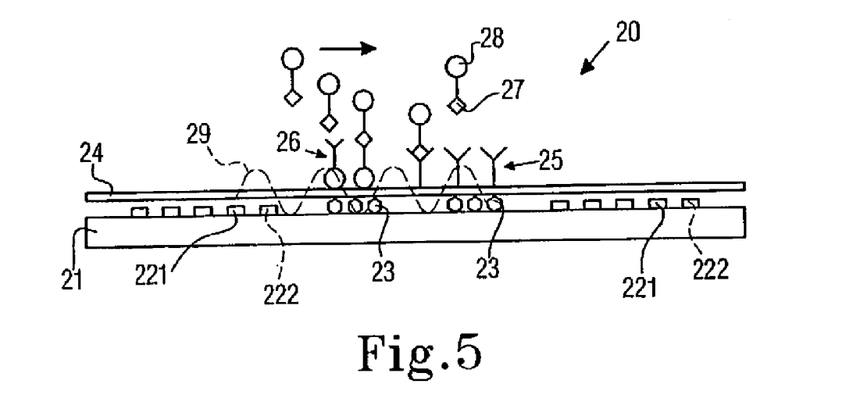
FIG. 5 is a schematic view, showing an enlarged cross-section along line V-V through a part of the chip as depicted in FIG. 4.

The patterns on the substrate are not limited to craters. For example, when using the device as an acoustic wave detector, one may produce matrices consisting of many interdigitated patterns needed for acoustic wave generation and detection. FIGS. 4 and 5 show one example of such a device.

The coils can be patterned using well-known techniques such as electroplating, vapour deposition or sputter.

In the following, non-limiting examples are described of how similar techniques, based on the magnetic manipulation of beads, can be used to enhance detection sensitivity of chemical reactions.

A single site of a matrix of Surface Acoustic Wave, SAW, devices are shown in FIGS. 4 and 5. Each device 20, includes an arrangement 22 for generating acoustic waves and magnetic field control means 23 on a substrate or carrier 21. The arrangement for generation and detection of acoustic waves includes two finger-shaped, reversed arranged conductors 221 and 222 provided on both sides of the control means 23. The control means 23 is arranged as a coil connected to a controller as described in conjunction with foregoing embodiment. The coil and the arrangement for generating acoustic waves are covered with an insulating layer 24 (see FIG. 5), made of, for example, glass or plastic, or a biomolecular layer. Onto this insulating layer, (biomolecular) "receptors" 25 can be adsorbed. The receptors, 25, can be used in their native state and adsorb spontaneously onto a suitably prepared insulating layer, 24. They may also be pre-adsorbed onto small magnetic beads, 23, and the whole complex (magnetic bead-receptor) can be attracted to the surface of the SAW device by magnetic field created by letting the current pass through the coil 23. The beads+ receptors attenuate the acoustic wave, 29, many times stronger compared to the case when native receptors are attached to the insulating layer 24 and thus much lower concentrations of adsorbents at the surface are needed when the receptor-bead complexes are adsorbed.

The magnetic beads are coated using a specific reagent (e.g. an antibody or a nucleic acid sequence) that is supposed to react with another reagent adsorbed on the surface of the sensor (e.g. an complementary antigene or a complementary sequence of nucleic acids). Only active sensor area is coated using reagent to be studied, the rest of the sensor (for example the electrode area, 221 in FIG. 4 is coated with the inert (non-reacting) coating. The coated beads are attracted to localities defined by the coils. The presence of the beads will enhance attenuation of an acoustic wave compared with the situation when the chemical reaction occurs between the two reagents only. Thus, the sensitivity of the device increases.

There are beads, however, that have been attracted to the surface by the magnetic field that did not undergo specific chemical reaction, or underwent another non-desirable reaction. These latter beads will produce "false" signals. One way to eliminate the undesirable signal is to wash away the beads, which in certain situations may be inconvenient, more difficult or time consuming. By using magnetic coils and/or external magnetic field, the undesired beads can be removed. One possibility to achieve this is simply to reverse the direction of current flowing in the coil. By carefully increasing current, it is possible to increase the magnetic field and repel loosely bound particles leaving only those having the desired bond.

Another advantage of such configuration is that it allows for the regeneration of the device. It may be possible to manufacture the surface of the insulating layer, 24, inert to receptors themselves, so that the receptor and bead complex is attached to the surface by magnetic forces acting on a bead. Once the investigation is completed the magnetic field can be removed (or the direction of the field changed using external magnet) causing the receptor and bead complex to desorb. This will leave the surface in its as-prepared state ready for another investigation.

If one wishes to study the reaction between these receptors and appropriate "donors", 27, the latter may be introduced in their native stage (27), or coupled to a magnetic bead 28.

FIGS. 2 and 3 illustrate a first example of an arrangement according to the invention. FIG. 2 illustrates an enlarged schematic view of a part of chip 19 comprising a number of sample collecting arrangements 10. Each sample collecting arrangement comprises a cavity (crater. pocket, well) 12 provided in a substrate 11 and means 13 to control the cap (lid, cover) 14. Each control means 13 is connected to controller 18 (FIG. 3) through connections 17. An on-chip detector (112) is also shown.

Figure 6A:
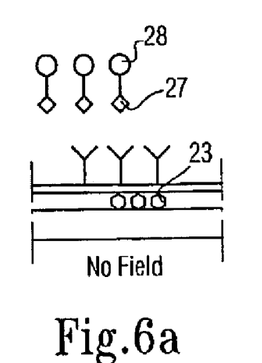
FIGS. 6A-6C illustrate different stages of detection in the arrangement of FIG. 5.
Figure 6B:
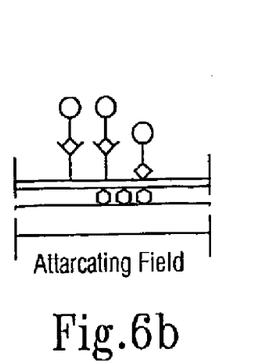
Figure 6C:
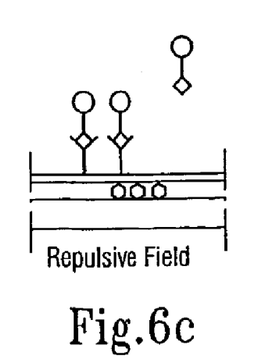

Since the beads influence the propagation of acoustic waves more strongly than do the molecules, which react to each other, one obtains manifold enhancement of the detection of the chemical reaction involving these molecules. One particular, but far from the only example of such reaction is the antibody-antigene reaction. Another example is the DNA-complementary DNA (or PNA) reaction. The reaction may occur spontaneously over many sites of the matrix, leaving other sites unreacted. By separately applying the magnetic field so as to remove particles from each site one obtains (i) a pattern over sites where reaction did take place, and (ii) a quantitative information about the number of reaction that did take place at each site (see FIGS. 6A-6C).

Another way to use the matrix with interdigitated electrodes is as a capacitor; a certain number of electrode pairs will be considered as a single site and will constitute a capacitor. One prepares each site of the matrix differently, i.e. using different chemistries. By directing beads, with specific molecules attached to them, to these sites using magnetic field, or withdrawing particles from these sites, one is able to perturb the dielectric constant of a layer close to the surface and therefore produce large changes of the capacitance of the device compared to attachment of only (bio) molecules.

A capacitance-measuring device may comprise the matrix of interdigitaded electrodes, similar to 221 and 222 in FIG. 4, but with a difference being that the sensing area is the area between the electrodes 221 and 222, and not in-between the electrode pairs (as in FIG. 4). One detects changes in capacitance (which is due to changes in the dielectric constant within the area where the electric field is between the electrodes is large) by measuring the chemical reaction induced changes of the electric field {changes in the AC-current and/or voltage as a function of frequency (or at a given frequency)} present between the 221 and 222 electrodes. For biological reagents submerged in the liquid, such changes are usually small since the dielectric constant of water and that of the reagents do not differ too much from each other. Use of magnetic beads would increase the sensitivity dramatically since the dielectric constant of a magnetic bead (metal) is infinite.

The use of magnetic beads may also enhance optical detection, for example optical absorbance of a fluid. Availability of beads introduces also a possibility to use other detection means such as plasmon resonance spectroscopy or photon correlation spectroscopy.

It is of importance to assure that the beads contributing to measurements in each of the cases above are the ones that have been responsible for the desirable chemistry.

The invention is not limited the shown embodiments, but can be varied in a number of ways without departing from the scope of the appended claims and the arrangement and the method can be implemented in various ways depending on application, functional units, needs and similar requirements.

The invention claimed is:

1. A sample preparing arrangement suitable for enhancing detection of different samples comprising a plurality of samples, said arrangement comprising:
    a carrier structure including a device for controllable generation of a magnetic field through a control signal that controls the device to generate the magnetic field to attract said plurality of samples towards specific locations on said carrier when connected to a first control signal, wherein said samples comprise magnetic particles;
    a controllable releasing force through a second control signal, wherein the controllable releasing force is a force for releasing a known number of the attracted samples; and
    a plurality of detection elements, wherein each of said detection elements is integrated in said carrier structure proximal to each of said specific locations, said detection elements enabling detection of localization of said plurality of samples relative to said specific locations.

2. The arrangement as recited in claim 1, wherein said device is a magnetically active material.

3. The arrangement as recited in claim 1, wherein said device is made of an electrically conducting material.

4. The arrangement as recited in claim 1, wherein said device comprises aluminum.

5. The arrangement as recited in claim 1, wherein said device comprises a plurality of coils for controllable generation of a magnetic field, and wherein a current of different strength is applied through a conductor to each of said plurality of coils.

6. The arrangement as recited in claim 1, wherein said device comprises a plurality of coils, and a known number of samples localized at each of the specific locations.

7. The arrangement as recited in claim 6, wherein a current amplitude and the number of windings in the coils are proportional to the strength of the magnetic field.

8. The arrangement as recited in claim 1, further comprising a cavity provided in the carrier structure.

9. The arrangement as recited in claim 8, further comprising a magnetic lid for capping said cavity.

10. The arrangement as recited in claim 9, wherein said magnetic lid comprises a bead, and magnetic material is deposited around said cavity, said bead being directed onto said cavity using external magnets that create magnetic fields counteracting a field created by the material deposited around each cavity.

11. The arrangement as recited in claim 9, wherein said lid is a micro-bead.

12. The arrangement as recited in claim 6, wherein said samples are attracted to predetermined specific locations when the plurality of coils proximal to said predetermined specific locations are energized by electric current to produce the magnetic fields of spatial attraction.

13. The arrangement as recited in claim 9, wherein at least one of said magnetic particles is in the cavity that is capped by the magnetic lid.

14. The arrangement as recited in claim 1, wherein said samples comprise magnetic particles carrying chemicals.

15. The arrangement as recited in claim 9, further comprising a control circuit that produces the attractive magnetic field, wherein said capping is detected by detecting a change in inductance in the control circuit, whereby the lid increases the inductance by acting as a magnetic yoke in a transformer.

16. The arrangement as recited in claim 13, wherein said detection elements detect changes of inductance when said magnetic particle passes into or out of said cavity, wherein a counted number of said particles passes into or out of said cavity, and the detection elements and control of the control signal enable counting of the number of samples passed into or out of said cavity.

17. The arrangement as recited in claim 16, wherein said detection is determined using the direction of externally controlled magnetic field by changing the direction of electric current flowing through a coil proximal to said cavity or flipping an external magnetic field.

18. The arrangement as recited in claim 16, wherein said particle includes a molecular coating, which reacts with a fluid in said cavity or with a coating adsorbed on walls of the cavity.

19. The arrangement as recited in claim 1, wherein said carrier structure comprises a substance selected from a group of substances consisting of: silicon, Si-compound, Si-oxide, Si-nitride, Si-carbide, a polymer, polyethylene, polyethylene glycol, polyethylene oxide, fluorine containing a polymer, silicon containing a polymer and combinations thereof.

20. The arrangement as recited in claim 1, further comprising a carrier substrate.

21. The arrangement as recited in claim 1, further comprising a member for generating acoustic waves, wherein said member is positioned on the carrier structure.

22. The arrangement as recited in claim 21, wherein said device and the member for generating acoustic waves are covered with an insulating layer constituting said carrier substrate.

23. The arrangement as recited in claim 22, wherein a combination of receptor-bead of a magnetizable material is attached on the insulating layer.

24. The arrangement as recited in claim 23, wherein a sample is provided with a magnetic portion attractive toward the receptor.

25. The arrangement as recited in claim 24, wherein said combination of receptor-bead attenuates the acoustic wave stronger than receptors attached to the insulating layer.

26. The arrangement as recited in claim 25, wherein a surface of the insulating layer is inert to receptors, and the receptor-bead combination is attached to the surface by magnetic forces acting on the bead.

27. The arrangement as recited in claim 1, further comprising a matrix of interdigitated electrodes, whereby one or more electrode pairs constitute a single site and a capacitor.

28. The arrangement as recited in claim 27, wherein each site of the matrix on the device comprises a different preparation, said preparations being prepared differently, by using different agents, and by directing beads, with specific molecules attached to them, to said sites using magnetic fields, or withdrawing particles from these sites, the dielectric constant of a layer close to the surface is perturbed and large changes of the capacitance of the device, compared to attachment of only a molecule, is detected.

29. The arrangement of claim 1, wherein said controllable releasing force comprises a force selected from a group of forces consisting of: gravitational force, shear force of flowing fluid, and magnetic force.

30. The arrangement of claim 1, wherein said controllable releasing force moves at least one of said attracted samples from a first specific location to a second specific location.

31. The arrangement of claim 1, wherein the samples comprise magnetic particles, said attraction transforming said particles from a spatially disordered state into a substantially ordered pattern.

* * * * *